United States Patent
Payen et al.

(10) Patent No.: US 12,139,704 B2
(45) Date of Patent: Nov. 12, 2024

(54) YEAST WITH IMPROVED ALCOHOL PRODUCTION UNDER HIGH DISSOLVED SOLIDS CONDITIONS

(71) Applicant: DANISCO US INC., Palo Alto, CA (US)

(72) Inventors: Celia Emily Gaby Payen, Wilmington, DE (US); Min Qi, Hockessin, DE (US)

(73) Assignee: DANISCO US INC., Palo Alto, CA (US)

( * ) Notice: Subject to any disclaimer, the term of this patent is extended or adjusted under 35 U.S.C. 154(b) by 1112 days.

(21) Appl. No.: 16/976,518

(22) PCT Filed: Mar. 4, 2019

(86) PCT No.: PCT/US2019/020564
§ 371 (c)(1),
(2) Date: Aug. 28, 2020

(87) PCT Pub. No.: WO2019/173225
PCT Pub. Date: Sep. 12, 2019

(65) Prior Publication Data
US 2021/0040474 A1   Feb. 11, 2021

Related U.S. Application Data

(60) Provisional application No. 62/639,252, filed on Mar. 6, 2018.

(51) Int. Cl.
*C12N 15/10* (2006.01)
*C12P 7/06* (2006.01)

(52) U.S. Cl.
CPC ............ *C12N 15/1024* (2013.01); *C12P 7/06* (2013.01)

(58) Field of Classification Search
None
See application file for complete search history.

(56) References Cited

U.S. PATENT DOCUMENTS

| | | |
|---|---|---|
| 8,795,998 B2 | 8/2014 | Pronk et al. |
| 8,956,851 B2 | 2/2015 | Argyros et al. |
| 9,175,270 B2 | 11/2015 | Nevoigt et al. |

FOREIGN PATENT DOCUMENTS

| | | |
|---|---|---|
| EP | 2060632 A1 | 5/2009 |
| EP | 2277989 A1 | 1/2011 |
| WO | 2014033019 A1 | 3/2014 |
| WO | 2015148272 A1 | 10/2015 |

OTHER PUBLICATIONS

Froquet et al., 2008. Control of Cellular Physiology by TM9 Proteins in Yeast and Dictyostelium. The Journal of Biological Chemistry vol. 283, No. 11, pp. 6764-6772 (Year: 2008).*

Gardner et al. Manipulating the Yeast Genome: Deletion, Mutation, and Tagging by PCR. Methods Mol Biol. 2014. vol. 1205: 45-78 (Year: 2014).*

International Search Report and Written Opinion from PCT Application No. PCT/US2019/020564 dated May 22, 2019, 13 pages.

Altschul et al., "Local Alignment Statistics", Meth. Enzymol., vol. 266, 1996, pp. 460-480.

Altschul et al., "Basic Local Alignment Search Tool", J. Mol. Biol., vol. 215, 1990, pp. 403-410.

Basso et al., "Engineering topology and kinetics of sucrose metabolism in *Saccharomyces cerevisiae* for improved ethanol yield", Metabolic Engineering Academies Press US, vol. 13, No. 6, Sep. 19, 2011, pp. 694-703.

Devereux et al., "A comprehensive set of sequence analysis programs for the VAX", Nucleic Acids Res., vol. 12, 1984, pp. 387-395.

Feng et al., "Progressive Sequence Alignment as a Prerequisite to Correct Phylogenetic Trees", J. Mol. Evol., vol. 25, 1987, pp. 351-360.

Froquet et al., "Control of cellular physiology by TM9 proteins in yeast and Dictyostelium", J. Biol. Chem., vol. 283, 2008, pp. 6764-6772.

Gombert et al., "Improving conversion yield of fermentable sugars into fuel ethanol in 1st generation yeast-based production processes", Curr. Opin. Biotechnol., vol. 33, 2015, pp. 81-86.

Henikoff et al., "Amino acid substitution matrices from protein blocks", Proc. Natl. Acad. Sci. USA, vol. 89, 1989, pp. 10915-10919.

Higgins et al., "Fast and sensitive multiple sequence alignments on a microcomputer", CABIOS, vol. 5, 1989, pp. 151-153.

Karlin et al., "Applications and statistics for multiple high-scoring segments in molecular sequences", Proc. Natl. Acad. Sci. USA, vol. 90, 1993, pp. 5873-5887.

Needleman et al., "A General Method Applicable to the Search for Similarities in the Amino Acid Sequence of Two Proteins", J. Mol. Biol. vol. 48, 1970, pp. 443-453.

Pearson et al., "Improved tools for biological sequence comparison", Proc. Natl Acad. Sci. USA, vol. 85, 1988, pp. 2444-2448.

Semkiv et al., "Increased ethanol accumulation from glucose via reduction of ATP level in a recombinant strain of *Saccharomyces cerevisiae* overexpressing alkaline phosphatase", BMC Biotechnology, Biomed Central Ltd., London, GB, vol. 14, No. 1, May 15, 2014, p. 42.

Smith et al., Adv. Appl. Math., "Comparison of Biosequences", vol. 2, 1981, pp. 482-489.

Thompson et al., "CLUSTAL W: improving the sensitivity of progressive multiple sequence alignment through sequence weighting, position-specific gap penalties and weight matrix choice", Nucleic Acids Res., vol. 22, 1994, pp. 4673-4680.

* cited by examiner

*Primary Examiner* — Celine X Qian
*Assistant Examiner* — Tiffany Nicole Grooms

(57) ABSTRACT

Described are compositions and methods relating to yeast cells having a genetic mutation that give rise to increased alcohol production, particularly under high dissolved solids growth conditions. Such yeast is well-suited for use in alcohol production to reduce fermentation time and/or increase yields.

19 Claims, No Drawings
Specification includes a Sequence Listing.

YEAST WITH IMPROVED ALCOHOL PRODUCTION UNDER HIGH DISSOLVED SOLIDS CONDITIONS

INCORPORATION BY REFERENCE OF THE SEQUENCE LISTING

The present application is being filed with a Sequence Listing in electronic format. The Sequence Listing is provided as an XML file entitled "2018306_NB41340USPSP_SeqListing_ST25.txt," created on Mar. 6, 2018, which is 9 KB in size. The information in the electronic format of the Sequence Listing is incorporated by reference in its entirety.

TECHNICAL FIELD

The present strains and methods relate to yeast having a genetic mutation that results in increased ethanol production, particularly under high dissolved solids growth conditions. Such yeast is well-suited for use in alcohol production to reduce fermentation time and/or increase yields.

BACKGROUND

Many countries make fuel alcohol from fermentable substrates, such as corn starch, sugar cane, cassava, and molasses. According to the Renewable Fuel Association (Washington DC, United States), 2015 fuel ethanol production was close to 15 billion gallons in the United States, alone.

In view of the large amount of alcohol produced in the world, even a minor increase in the efficiency of a fermenting organism can result in a tremendous increase in the amount of available alcohol. Accordingly, the need exists for organisms that are more efficient at producing alcohol.

SUMMARY

Described are methods relating to modified yeast cells capable of increased alcohol production, particularly under high dissolved solids growth conditions. Aspects and embodiments of the compositions and methods are described in the following, independently-numbered paragraphs.

1. In one aspect, modified yeast cells derived from parental yeast cells are provided, the modified cells comprising a genetic alteration that causes the modified cells to produce a decreased amount of functional TMN2 polypeptide compared to the parental cells, wherein the modified cells produce during fermentation an increased amount of ethanol compared to parental cells under equivalent fermentation conditions.
2. In some embodiments of the modified cells of paragraph 1, the genetic alteration comprises a disruption of a YDR107C gene present in the parental cells.
3. In some embodiments of the modified cells of paragraph 2, disruption of a YDR107C gene is the result of deletion of all or part of a YDR107C gene.
4. In some embodiments of the modified cells of paragraph 2, disruption of a YDR107C gene is the result of deletion of a portion of genomic DNA comprising a YDR107C gene.
5. In some embodiments of the modified cells of paragraph 2, disruption of a YDR107C gene is the result of mutagenesis of a YDR107C gene.
6. In some embodiments of the modified cells of any of paragraphs 2-5, disruption of a YDR107C gene is performed in combination with introducing a gene of interest at the genetic locus of a YDR107C gene.
7. In some embodiments of the modified cells of any of paragraphs 1-6, the cells do not produce functional TMN2 polypeptides.
8. In some embodiments of the modified cells of any of paragraphs 1-6, the cells do not produce TMN2 polypeptides.
9. In some embodiments, the modified cells of any of paragraphs 1-8 further comprise an exogenous gene encoding a carbohydrate processing enzyme.
10. In some embodiments, the modified cells of any of paragraphs 1-9 further comprise an alteration in the glycerol pathway and/or the acetyl-CoA pathway.
11. In some embodiments, the modified cells of any of paragraphs 1-10 further comprise an alternative pathway for making ethanol.
12. In some embodiments of the modified cells of any of paragraphs 1-11, the cells are of a *Saccharomyces* spp.
13. In some embodiments of the modified cells of any of paragraphs 1-12, the amount of ethanol produced by the modified yeast cells and the parental yeast cells is measured at 24 hours following inoculation of a hydrolyzed starch substrate comprising 34-36% dissolved solids and having a pH of 4.8-5.4.
14. In another aspect, a method for producing a modified yeast cell is provided, comprising: introducing a genetic alteration into a parental yeast cell, which genetic alteration reduces or prevents the production of functional TMN2 polypeptide compared to the parental cells, thereby producing modified cells that produces during fermentation an increased amount of ethanol compared to the parental cells under equivalent fermentation conditions.
15. In some embodiments of the method of paragraph 14, the genetic alteration comprises disrupting a YDR107C gene in the parental cells by genetic manipulation.
16. In some embodiments of the method of paragraph 14 or 15, the genetic alteration comprises deleting a YDR107C gene in the parental cells using genetic manipulation.
17. In some embodiments of the method of any of paragraphs 14-16, disruption of a YDR107C gene is performed in combination with introducing a gene of interest at the genetic locus of a YDR107C gene.
18. In some embodiments of the method of any of paragraphs 14-17, disruption of a YDR107C gene is performed in combination with making an alteration in the glycerol pathway and/or the acetyl-CoA pathway.
19. In some embodiments of the method of any of paragraphs 14-18, disruption of a YDR107C gene is performed in combination with adding an alternative pathway for making ethanol.
20. In some embodiments of the method of any of paragraphs 14-19, disruption of a YDR107C gene is performed in combination with introducing an exogenous gene encoding a carbohydrate processing enzyme.
21. In some embodiments of the method of any of paragraphs 14-20, the modified cell is from a *Saccharomyces* spp.
22. In some embodiments of the method of any of paragraphs 14-21, the amount of ethanol produced by the modified yeast cells and the parental yeast cells is measured at 24 hours following inoculation of a hydrolyzed starch substrate comprising 34-36% dissolved solids and having a pH of 4.8-5.4.

23. In another aspect, modified yeast cells produced by the method of any of paragraphs 14-22 are provided.

These and other aspects and embodiments of present modified cells and methods will be apparent from the description.

DETAILED DESCRIPTION

I. Overview

The present compositions and methods relate to modified yeast cells demonstrating increased ethanol production, particularly under high dissolved solids growth conditions, compared to their parental cells. When used for ethanol production, the modified cells allow for increased yields and or shorter fermentation times, thereby increasing the supply of ethanol for world consumption.

II. Definitions

Prior to describing the present strains and methods in detail, the following terms are defined for clarity. Terms not defined should be accorded their ordinary meanings as used in the relevant art.

As used herein, "alcohol" refer to an organic compound in which a hydroxyl functional group (—OH) is bound to a saturated carbon atom.

As used herein, "butanol" refers to the butanol isomers 1-butanol, 2-butanol, tert-butanol, and/or isobutanol (also known as 2-methyl-1-propanol) either individually or as mixtures thereof.

As used herein, "yeast cells" yeast strains, or simply "yeast" refer to organisms from the phyla Ascomycota and Basidiomycota. Exemplary yeast is budding yeast from the order Saccharomycetales. Particular examples of yeast are *Saccharomyces* spp., including but not limited to *S. cerevisiae*. Yeast include organisms used for the production of fuel alcohol as well as organisms used for the production of potable alcohol, including specialty and proprietary yeast strains used to make distinctive-tasting beers, wines, and other fermented beverages.

As used herein, the phrase "variant yeast cells," "modified yeast cells," or similar phrases (see above), refer to yeast that include genetic modifications and characteristics described herein. Variant/modified yeast do not include naturally occurring yeast.

As used herein, the phrase "substantially free of an activity," or similar phrases, means that a specified activity is either undetectable in an admixture or present in an amount that would not interfere with the intended purpose of the admixture.

As used herein, the terms "polypeptide" and "protein" (and their respective plural forms) are used interchangeably to refer to polymers of any length comprising amino acid residues linked by peptide bonds. The conventional one-letter or three-letter codes for amino acid residues are used herein and all sequence are presented from an N-terminal to C-terminal direction. The polymer can be linear or branched, it can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

As used herein, functionally and/or structurally similar proteins are considered to be "related proteins." Such proteins can be derived from organisms of different genera and/or species, or even different classes of organisms (e.g., bacteria and fungi). Related proteins also encompass homologs determined by primary sequence analysis, determined by secondary or tertiary structure analysis, or determined by immunological cross-reactivity.

As used herein, the term "homologous protein" refers to a protein that has similar activity and/or structure to a reference protein. It is not intended that homologs necessarily be evolutionarily related. Thus, it is intended that the term encompass the same, similar, or corresponding enzyme(s) (i.e., in terms of structure and function) obtained from different organisms. In some embodiments, it is desirable to identify a homolog that has a quaternary, tertiary and/or primary structure similar to the reference protein. In some embodiments, homologous proteins induce similar immunological response(s) as a reference protein. In some embodiments, homologous proteins are engineered to produce enzymes with desired activity(ies).

The degree of homology between sequences can be determined using any suitable method known in the art (see, e.g., Smith and Waterman (1981) *Adv. Appl. Math.* 2:482; Needleman and Wunsch (1970) *J Mol. Biol.,* 48:443; Pearson and Lipman (1988) *Proc. Natl. Acad. Sci. USA* 85:2444; programs such as GAP, BESTFIT, FASTA, and TFASTA in the Wisconsin Genetics Software Package (Genetics Computer Group, Madison, WI); and Devereux et al. (1984) *Nucleic Acids Res.* 12:387-95).

For example, PILEUP is a useful program to determine sequence homology levels. PILEUP creates a multiple sequence alignment from a group of related sequences using progressive, pair-wise alignments. It can also plot a tree showing the clustering relationships used to create the alignment. PILEUP uses a simplification of the progressive alignment method of Feng and Doolittle, (Feng and Doolittle (1987) *J. Mol. Evol.* 35:351-60). The method is similar to that described by Higgins and Sharp ((1989) *CABIOS* 5:151-53). Useful PILEUP parameters including a default gap weight of 3.00, a default gap length weight of 0.10, and weighted end gaps. Another example of a useful algorithm is the BLAST algorithm, described by Altschul et al. ((1990) *J. Mol. Biol.* 215:403-10) and Karlin et al. ((1993) *Proc. Natl. Acad. Sci. USA* 90:5873-87). One particularly useful BLAST program is the WU-BLAST-2 program (see, e.g., Altschul et al. (1996) *Meth. Enzymol.* 266:460-80). Parameters "W," "T," and "X" determine the sensitivity and speed of the alignment. The BLAST program uses as defaults a word-length (W) of 11, the BLOSUM62 scoring matrix (see, e.g., Henikoff and Henikoff (1989) *Proc. Natl. Acad. Sci. USA* 89:10915) alignments (B) of 50, expectation (E) of 10, M'S, N'-4, and a comparison of both strands.

As used herein, the phrases "substantially similar" and "substantially identical," in the context of at least two nucleic acids or polypeptides, typically means that a polynucleotide or polypeptide comprises a sequence that has at least about 70% identity, at least about 75% identity, at least about 80% identity, at least about 85% identity, at least about 90% identity, at least about 91% identity, at least about 92% identity, at least about 93% identity, at least about 94% identity, at least about 95% identity, at least about 96% identity, at least about 97% identity, at least about 98% identity, or even at least about 99% identity, or more, compared to the reference (i.e., wild-type) sequence. Percent sequence identity is calculated using CLUSTAL W algorithm with default parameters. See Thompson et al. (1994) *Nucleic Acids Res.* 22:4673-4680. Default parameters for the CLUSTAL W algorithm are:

Gap opening penalty: 10.0
Gap extension penalty: 0.05
Protein weight matrix: BLOSUM series
DNA weight matrix: IUB
Delay divergent sequences %: 40
Gap separation distance: 8
DNA transitions weight: 0.50
List hydrophilic residues: GPSNDQEKR
Use negative matrix: OFF
Toggle Residue specific penalties: ON
Toggle hydrophilic penalties: ON
Toggle end gap separation penalty OFF.

Another indication that two polypeptides are substantially identical is that the first polypeptide is immunologically cross-reactive with the second polypeptide. Typically, polypeptides that differ by conservative amino acid substitutions are immunologically cross-reactive. Thus, a polypeptide is substantially identical to a second polypeptide, for example, where the two peptides differ only by a conservative substitution. Another indication that two nucleic acid sequences are substantially identical is that the two molecules hybridize to each other under stringent conditions (e.g., within a range of medium to high stringency).

As used herein, the term "gene" is synonymous with the term "allele" in referring to a nucleic acid that encodes and directs the expression of a protein or RNA. Vegetative forms of filamentous fungi are generally haploid, therefore a single copy of a specified gene (i.e., a single allele) is sufficient to confer a specified phenotype.

As used herein, the terms "wild-type" and "native" are used interchangeably and refer to genes proteins or strains found in nature.

As used herein, the term "protein of interest" refers to a polypeptide that is desired to be expressed in modified yeast. Such a protein can be an enzyme, a substrate-binding protein, a surface-active protein, a structural protein, a selectable marker, or the like, and can be expressed at high levels. The protein of interest is encoded by a modified endogenous gene or a heterologous gene (i.e., gene of interest") relative to the parental strain. The protein of interest can be expressed intracellularly or as a secreted protein.

As used herein, "deletion of a gene," refers to its removal from the genome of a host cell. Where a gene includes control elements (e.g., enhancer elements) that are not located immediately adjacent to the coding sequence of a gene, deletion of a gene refers to the deletion of the coding sequence, and optionally adjacent enhancer elements, including but not limited to, for example, promoter and/or terminator sequences, but does not require the deletion of non-adjacent control elements.

As used herein, "disruption of a gene" refers broadly to any genetic or chemical manipulation, i.e., mutation, that substantially prevents a cell from producing a function gene product, e.g., a protein, in a host cell. Exemplary methods of disruption include complete or partial deletion of any portion of a gene, including a polypeptide-coding sequence, a promoter, an enhancer, or another regulatory element, or mutagenesis of the same, where mutagenesis encompasses substitutions, insertions, deletions, inversions, and combinations and variations, thereof, any of which mutations substantially prevent the production of a function gene product. A gene can also be disrupted using RNAi, antisense, or any other method that abolishes gene expression. A gene can be disrupted by deletion or genetic manipulation of non-adjacent control elements.

As used herein, the terms "genetic manipulation" and "genetic alteration" are used interchangeably and refer to the alteration/change of a nucleic acid sequence. The alteration can include but is not limited to a substitution, deletion, insertion or chemical modification of at least one nucleic acid in the nucleic acid sequence.

As used herein, a "primarily genetic determinant" refers to a gene, or genetic manipulation thereof, that is necessary and sufficient to confer a specified phenotype in the absence of other genes, or genetic manipulations, thereof. However, that a particular gene is necessary and sufficient to confer a specified phenotype does not exclude the possibility that additional effects to the phenotype can be achieved by further genetic manipulations.

As used herein, a "functional polypeptide/protein" is a protein that possesses an activity, such as an enzymatic activity, a binding activity, a surface-active property, or the like, and which has not been mutagenized, truncated, or otherwise modified to abolish or reduce that activity. Functional polypeptides can be thermostable or thermolabile, as specified.

As used herein, "a functional gene" is a gene capable of being used by cellular components to produce an active gene product, typically a protein. Functional genes are the antithesis of disrupted genes, which are modified such that they cannot be used by cellular components to produce an active gene product, or have a reduced ability to be used by cellular components to produce an active gene product.

As used herein, yeast cells have been "modified to prevent the production of a specified protein" if they have been genetically or chemically altered to prevent the production of a functional protein/polypeptide that exhibits an activity characteristic of the wild-type protein. Such modifications include, but are not limited to, deletion or disruption of the gene encoding the protein (as described, herein), modification of the gene such that the encoded polypeptide lacks the aforementioned activity, modification of the gene to affect post-translational processing or stability, and combinations, thereof.

As used herein, "attenuation of a pathway" or "attenuation of the flux through a pathway" i.e., a biochemical pathway, refers broadly to any genetic or chemical manipulation that reduces or completely stops the flux of biochemical substrates or intermediates through a metabolic pathway. Attenuation of a pathway may be achieved by a variety of well-known methods. Such methods include but are not limited to: complete or partial deletion of one or more genes, replacing wild-type alleles of these genes with mutant forms encoding enzymes with reduced catalytic activity or increased Km values, modifying the promoters or other regulatory elements that control the expression of one or more genes, engineering the enzymes or the mRNA encoding these enzymes for a decreased stability, misdirecting enzymes to cellular compartments where they are less likely to interact with substrate and intermediates, the use of interfering RNA, and the like.

As used herein, "aerobic fermentation" refers to growth in the presence of oxygen.

As used herein, "anaerobic fermentation" refers to growth in the absence of oxygen.

As used herein, the singular articles "a," "an," and "the" encompass the plural referents unless the context clearly dictates otherwise. All references cited herein are hereby incorporated by reference in their entirety. The following abbreviations/acronyms have the following meanings unless otherwise specified:

° C. degrees Centigrade
AA α-amylase
bp base pairs
DNA deoxyribonucleic acid
DP degree of polymerization
ds or DS dry solids
EtOH ethanol
g or gm gram
g/L grams per liter
GA glucoamylase
GAU/g ds glucoamylase units per gram dry solids
$H_2O$ water
HPLC high performance liquid chromatography
hr or h hour
kg kilogram
M molar
mg milligram
mL or ml milliliter
ml/min milliliter per minute
mM millimolar
N normal
nm nanometer
PCR polymerase chain reaction
ppm parts per million
SAPU/g ds protease units per gram dry solids
SSCU/g ds fungal alpha-amylase units per gram dry solids
Δ relating to a deletion
μg microgram
μL and μl microliter
μM micromolar

III. Modified Yeast Cells Expressing Reduced Levels of TMN2 Polypeptides

In one aspect, modified yeast cells are provided, the modified yeast having a genetic alteration that causes the cells of the modified strain to produce a decreased amount of functional Transmembrane Family 9 (TM9) Superfamily polypeptides compared to the otherwise-identical parental cells. The TM9 Superfamily, which includes three members, is a conserved group of transmembrane proteins believed to be part of a nutrient-controlled signaling cascade that ultimately controls cellular adhesion (Froquet, R. (2008) *J. Biol. Chem.* 283:6764-72). Strains lacking any member of the family are suppressed for adhesive growth under conditions of nitrogen starvation (Ibid.).

Applicants have discovered that yeast having a genetic alteration that reduces TMN2 polypeptide production demonstrate increased ethanol production in fermentations, allowing for higher yields, shorter fermentation times or both. The effect is most prominent under condition of high dissolved solids. Shorter fermentation times allow alcohol production facilities to run more fermentation in a given period of time, increasing productivity. Shorter fermentation times and higher fermentation temperatures also reduce the risk of contamination during fermentation and, depending on ambient conditions, reduce the need to cool the fermentation reaction to maintain the viability of the yeast.

The reduction in the amount of functional TMN2 polypeptides can result from disruption of a gene encoding a TMN2 polypeptide (i.e., YDR107C) present in the parental strain. Because disruption of a YDR107C gene is a primary genetic determinant for conferring the increased ethanol-production-phenotype to the modified cells, in some embodiments the modified cells need only comprise a disrupted YDR107C gene, while all other genes can remain intact. In other embodiments, the modified cells can optionally include additional genetic alterations compared to the parental cells from which they are derived. While such additional genetic alterations are not necessary to confer the described phenotype, they may confer other advantages to the modified cells.

Disruption of a YDR107C gene can be performed using any suitable methods that substantially prevent expression of a function TMN2 polypeptide. Exemplary methods of disruption as are known to one of skill in the art include but are not limited to: complete or partial deletion of a YDR107C gene, including complete or partial deletion of, e.g., a TMN2-coding sequence, the promoter, the terminator, an enhancer, or another regulatory element; and complete or partial deletion of a portion of the chromosome that includes any portion of a YDR107C gene. Particular methods of disrupting a YDR107C gene include making nucleotide substitutions or insertions in any portion of a YDR107C gene, e.g., a TMN2-coding sequence, the promoter, the terminator, an enhancer, or another regulatory element. Preferably, deletions, insertions, and/or substitutions (collectively referred to as mutations) are made by genetic manipulation using sequence-specific molecular biology techniques, as opposed to by chemical mutagenesis, which is generally not targeted to specific nucleic acid sequences. Nonetheless, chemical mutagenesis can, in theory, be used to disrupt a YDR107C gene.

Mutations in a YDR107C gene can reduce the efficiency of a YDR107C promoter, reduce the efficiency of a YDR107C enhancer, interfere with the splicing or editing of a YDR107C mRNA, interfere with the translation of a YDR107C mRNA, introduce a stop codon into a TMN2-coding sequence to prevent the translation of full-length TMN2 protein, change the coding sequence of a TMN2 protein to produce a less active or inactive protein or reduce TMN2 interaction with other proteins, or DNA, change the coding sequence of a TMN2 protein to produce a less stable protein or target the protein for destruction, cause a TMN2 protein to misfold or be incorrectly modified (e.g., by glycosylation), or interfere with cellular trafficking of a TMN2 protein. In some embodiments, these and other genetic manipulations act to reduce or prevent the expression of a functional TMN2 protein, or reduce or prevent the normal function of TMN2. In some embodiments, the present modified cells include genetic manipulations that reduce or prevent membrane insertion of TMN2.

In some embodiments, the decrease in the amount of functional TMN2 polypeptide in the modified cells is a decrease of at least 30%, at least 40%, at least 50%, at least 60%, at least 70%, at least 80%, at least 90%, at least 95%, at least 98%, at least 99%, or more, compared to the amount of functional TMN2 polypeptide in parental cells growing under the same conditions. In some embodiments, the reduction of expression of functional TMN2 protein in the modified cells is a reduction of at least 30%, at least 40%, at least 50%, at least 60%, at least 70%, at least 80%, at least 90%, at least 95%, at least 98%, at least 99%, or more, compared to the amount of functional TMN2 polypeptide in parental cells growing under the same conditions.

In some embodiments, the increase in alcohol in the modified cells is an increase of at least 1%, at least 2%, at least 3%, at least 4%, at least 5%, or more, compared to the amount of alcohol produced in parental cells growing under the same conditions.

Preferably, disruption of a YDR107C gene is performed by genetic manipulation using sequence-specific molecular biology techniques, as opposed to chemical mutagenesis, which is generally not targeted to specific nucleic acid sequences. However, chemical mutagenesis is not excluded as a method for making modified yeast cells.

In some embodiments, the parental cell that is modified already includes a gene of interest, such as a gene encoding a selectable marker, carbohydrate-processing enzyme, or other polypeptide. In some embodiments, a gene of introduced is subsequently introduced into the modified cells.

The amino acid sequence of the exemplified S. cerevisiae Tmn2 polypeptide (i.e., TM9 member 2; usually referred to as TMN2 or TMN2p) is shown, below, as SEQ ID NO: 1:

```
  1 MKRGVWLLIY CYATLTKGFS LPGLSPTTYH SGDEIPLLVN RLTPSIYFQH QDEEGNDVSG

61 DKEHFLYSYD YYNKRFHFCR PEHVEKQPES LGSVIFGDRI YNSPFQLNML EEKECVALCK

121 STIPGKDAKF INTLIKSGFF QNWLVDGLPA ARKAYDSRTK TNYYGTGFEL GFTDVKQTVD

181 GKAVPSTMEE LTSEASNEDV ILDARLPKNV KPNLVKTVEL PYFVNHFDIE VEFHDRGNDN

241 YRVVGVIVNP VSIERSSPGA CSTTGKPLIL DEDKDNEVYF TYSVKFVASD TVWATRWDKY

301 LHIYDPQIQW FSLINFSVIV ILLSSVVMHS LLRALKSDLA RYNELNLDNE FHEDSGWKLG

361 HGDVFRTPSK SMLLSILVGS GMQLFLMVMC SIFFAAVGLV SPVSRGSLPT VMFVLYALFG

421 FVGSYASMGV YKFFRGPYWK ANMILTPILL PGAIFLLIVI MNFFLLFAHS SGVIPARSLF

481 FIILLWFLVS VPLSFAGSIV AHKQCNWDEH PTKTNQIARQ IPYQPWYLRT AQATLIAGIF

541 SFGSIAVELY FIYSSLWFNK IFYMFGFLLF SFLLLTLTTS LVTILITYYS LCLENWLWQW

601 RSFIIGGLGC SIYTFIHSIL FTKFKLGGVI TVVLYLGYSL IISALCCVVT GAIGFFSSMF

661 FIRKIYSAIK VE*
```

Based on a BLAST search of the NCBI protein database, the described TMN2 polypeptide is 100% identical to at least ten deposits:

TABLE 1

SEQ ID NO: 1 compared to other S. cerevisiae TMN2 polypeptides

| Description | E value | % Identity | GenBank Accession No. |
| --- | --- | --- | --- |
| TMN2p [S. cerevisiae S288c] | 2.8E−79 | 100% | NP_010439.1 |
| TMN2p [S. cerevisiae VL3] | 2.8E−79 | 100% | EGA87502.1 |
| TMN2p [S. cerevisiae AVRI796] | 2.8E−79 | 100% | EGA75445.1 |
| TMN2p [S. cerevisiae RM11-1a] | 2.8E−79 | 100% | EDV08157.1 |
| TMN2p [S. cerevisiae Kyokai No. 7] | 2.8E−79 | 100% | GAA22386.1 |
| TMN2p [S. cerevisiae JAY291] | 2.8E−79 | 100% | EEU04638.1.1 |
| TMN2p [S. cerevisiae FostersO] | 2.8E−79 | 100% | EGA63002.1 |
| TMN2p [S. cerevisiae YJM789] | 2.8E−79 | 100% | EDN60494.1 |
| TMN2p [S. cerevisiae Vin13] | 2.8E−79 | 100% | EGA79484.1 |
| TMN2p [S. cerevisiae CEN.PK113-7D] | 2.8E−79 | 100% | EIW11359.1 |

It is expected that the present compositions and methods are applicable to other structurally similar TMN2 polypeptides, as well as other related proteins, homologs, and functionally similar polypeptides.

In some embodiments of the present compositions and methods, the amino acid sequence of the Tmn2 protein that is altered in production levels has a specified degree of overall amino acid sequence identity to the amino acid sequence of SEQ ID NO: 1, e.g., at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or even at least about 99% identity, to SEQ ID NO: 1.

In some embodiments of the present compositions and methods, the YDR107C gene that is disrupted encodes a Tmn2 protein that has a specified degree of overall amino acid sequence identity to the amino acid sequence of SEQ ID NO: 1, e.g., at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or even at least about 99% identity, to SEQ ID NO: 1.

The amino acid sequence information provided, herein, readily allows the skilled person to identify a Tmn2 protein, and the nucleic acid sequence encoding a Tmn2 protein, in any yeast, and to make appropriate disruptions in a TMN2 gene to affect the production of the Tmn2 protein.

In some embodiments, the decrease in the amount of functional Tmn2 polypeptide in the modified cells is a decrease of at least 30%, at least 40%, at least 50%, at least 60%, at least 70%, at least 80%, at least 90%, at least 95%, at least 98%, at least 99%, or more, compared to the amount of functional Tmn2 polypeptide in parental cells growing under the same conditions. In some embodiments, the reduction of expression of functional Tmn2 protein in the modified cells is a reduction of at least 30%, at least 40%, at least 50%, at least 60%, at least 70%, at least 80%, at least 90%, at least 95%, at least 98%, at least 99%, or more, compared to the amount of functional Tmn2 polypeptide in parental cells growing under the same conditions.

In some embodiments, the increase in ethanol production by the modified cells, compared to otherwise identical parental cells, is an increase of at least 0.2%, at least 0.4%, at least 0.6%, at least 0.8%, at least 1.0%, at least 1.2%, at least 1.4%, at least 1.6%, at least 1.8%, at least 2.0% or more.

IV. Combination of Decreased TM9 Expression with Other Mutations that Affect Alcohol Production In some embodiments, in addition to expressing decreased amounts of TMN2 polypeptides, the present modified yeast cells further include additional modifications that affect ethanol production.

In particular embodiments the modified yeast cells include an artificial or alternative ethanol-producing pathway resulting from the introduction of a heterologous phosphoketolase (PKL) gene, a heterologous phosphotransacetylase (PTA) gene and a heterologous acetylating acetyl dehydrogenase (AADH), as described in WO2015148272 (Miasnikov et al.), to channel carbon flux away from the glycerol pathway and toward the synthesis of acetyl-CoA, which is then converted to ethanol.

The modified cells may further include mutations that result in attenuation of the native glycerol biosynthesis pathway, which are known to increase alcohol production. Methods for attenuation of the glycerol biosynthesis pathway in yeast are known and include reduction or elimination of endogenous NAD-dependent glycerol 3-phosphate dehydrogenase (GPD) or glycerol phosphate phosphatase activity (GPP), for example by disruption of one or more of the genes GPD1, GPD2, GPP1 and/or GPP2. See, e.g., U.S. Pat. No. 9,175,270 (Elke et al.), U.S. Pat. No. 8,795,998 (Pronk et al.) and U.S. Pat. No. 8,956,851 (Argyros et al.).

The modified yeast may further feature increased acetyl-CoA synthase (also referred to acetyl-CoA ligase) activity (EC 6.2.1.1) to scavenge (i.e., capture) acetate produced by chemical or enzymatic hydrolysis of acetyl-phosphate (or present in the culture medium of the yeast for any other reason) and converts it to Ac-CoA. This avoids the undesirable effect of acetate on the growth of yeast cells and may further contribute to an improvement in alcohol yield. Increasing acetyl-CoA synthase activity may be accomplished by introducing a heterologous acetyl-CoA synthase gene into cells, increasing the expression of an endogenous acetyl-CoA synthase gene and the like. A particularly useful acetyl-CoA synthase for introduction into cells can be obtained from *Methanosaeta concilii* (UniProt/TrEMBL Accession No.: WP 013718460). Homologs of this enzymes, including enzymes having at least 85%, at least 90%, at least 92%, at least 95%, at least 97%, at least 98% and even at least 99% amino acid sequence identity to the aforementioned acetyl-CoA synthase from *Methanosaeta concilii*, are also useful in the present compositions and methods.

In some embodiments the modified cells may further include a heterologous gene encoding a protein with NADt-dependent acetylating acetaldehyde dehydrogenase activity and/or a heterologous gene encoding a pyruvate-formate lyase. The introduction of such genes in combination with attenuation of the glycerol pathway is described, e.g., in U.S. Pat. No. 8,795,998 (Pronk et al.).

In some embodiments, the present modified yeast cells further comprise a butanol biosynthetic pathway. In some embodiments, the butanol biosynthetic pathway is an isobutanol biosynthetic pathway. In some embodiments, the isobutanol biosynthetic pathway comprises a polynucleotide encoding a polypeptide that catalyzes a substrate to product conversion selected from the group consisting of: (a) pyruvate to acetolactate; (b) acetolactate to 2,3-dihydroxyisovalerate; (c) 2,3-dihydroxyisovalerate to 2-ketoisovalerate; (d) 2-ketoisovalerate to isobutyraldehyde; and (e) isobutyraldehyde to isobutanol. In some embodiments, the isobutanol biosynthetic pathway comprises polynucleotides encoding polypeptides having acetolactate synthase, keto acid reductoisomerase, dihydroxy acid dehydratase, ketoisovalerate decarboxylase, and alcohol dehydrogenase activity.

In some embodiments, the modified yeast cells comprising a butanol biosynthetic pathway further comprise a modification in a polynucleotide encoding a polypeptide having pyruvate decarboxylase activity. In some embodiments, the yeast cells comprise a deletion, mutation, and/or substitution in an endogenous polynucleotide encoding a polypeptide having pyruvate decarboxylase activity. In some embodiments, the polypeptide having pyruvate decarboxylase activity is selected from the group consisting of: PDC1, PDC5, PDC6, and combinations thereof. In some embodiments, the yeast cells further comprise a deletion, mutation, and/or substitution in one or more endogenous polynucleotides encoding FRA2, ALD6, ADH1, GPD2, BDH1, and YMR226C.

GOI Section

V. Combination of Decreased TMN2 Expression with Other Beneficial Mutations

In some embodiments, in addition to expressing reduced amounts of TMN2 polypeptides, optionally in combination with other genetic modifications that benefit alcohol production, the present modified yeast cells further include any number of additional genes of interest encoding proteins of interest. Additional genes of interest may be introduced before, during, or after genetic manipulations that result in reduced expression of TMN2 polypeptides. Proteins of interest, include selectable markers, carbohydrate-processing enzymes, and other commercially-relevant polypeptides, including but not limited to an enzyme selected from the group consisting of a dehydrogenase, a transketolase, a phosphoketolase, a transladolase, an epimerase, a phytase, a xylanase, a β-glucanase, a phosphatase, a protease, an α-amylase, a β-amylase, a glucoamylase, a pullulanase, an isoamylase, a cellulase, a trehalase, a lipase, a pectinase, a polyesterase, a cutinase, an oxidase, a transferase, a reductase, a hemicellulase, a mannanase, an esterase, an isomerase, a pectinases, a lactase, a peroxidase and a laccase. Proteins of interest may be secreted, glycosylated, and otherwise-modified.

VI. Yeast Cells Suitable for Modification

Yeasts are unicellular eukaryotic microorganisms classified as members of the fungus kingdom and include organisms from the phyla Ascomycota and Basidiomycota. Yeast that can be used for alcohol production include, but are not limited to, *Saccharomyces* spp., including *S. cerevisiae*, as well as *Kluyveromyces, Lachancea* and *Schizosaccharomyces* spp. Numerous yeast strains are commercially available, many of which have been selected or genetically engineered for desired characteristics, such as high alcohol production, rapid growth rate, and the like. Some yeasts have been genetically engineered to produce heterologous enzymes, such as glucoamylase or α-amylase.

VII. Substrates and Products

Alcohol production from a number of carbohydrate substrates, including but not limited to corn starch, sugar cane, cassava, and molasses, is well known, as are innumerable variations and improvements to enzymatic and chemical conditions and mechanical processes. The present compositions and methods are believed to be fully compatible with such substrates and conditions.

Alcohol fermentation products include organic compound having a hydroxyl functional group (—OH) is bound to a carbon atom. Exemplary alcohols include but are not limited to methanol, ethanol, n-propanol, isopropanol, n-butanol, isobutanol, n-pentanol, 2-pentanol, isopentanol, and higher alcohols. The most commonly made fuel alcohols are ethanol, and butanol.

These and other aspects and embodiments of the present strains and methods will be apparent to the skilled person in view of the present description. The following examples are intended to further illustrate, but not limit, the strains and methods.

Examples

Example 1. Deletion of YDR107c in *Saccharomyces cerevisiae*

Genetic screening was performed to identify *S. cerevisiae* mutants capable of improved ethanol production after 24 hours of fermentation, and a number of candidate genes were identified and selected for further testing (data not shown). One of the genes selected for further analysis was YDR107C, which encodes TMN2. The amino acid sequence of TMN2 is provided below as SEQ ID NO: 1:

```
  1 MKRGVWLLIY CYATLTKGFS LPGLSPTTYH SGDEIPLLVN RLTPSIYFQH QDEEGNDVSG

61 DKEHFLYSYD YYNKRFHFCR PEHVEKQPES LGSVIFGDRI YNSPFQLNML EEKECVALCK

121 STIPGKDAKF INTLIKSGFF QNWLVDGLPA ARKAYDSRTK TNYYGTGFEL GFTDVKQTVD

181 GKAVPSTMEE LTSEASNEDV ILDARLPKNV KPNLVKTVEL PYFVNHFDIE VEFHDRGNDN

241 YRVVGVIVNP VSIERSSPGA CSTTGKPLIL DEDKDNEVYF TYSVKFVASD TVWATRWDKY

301 LHIYDPQIQW FSLINFSVIV ILLSSVVMHS LLRALKSDLA RYNELNLDNE FHEDSGWKLG

361 HGDVFRTPSK SMLLSILVGS GMQLFLMVMC SIFFAAVGLV SPVSRGSLPT VMFVLYALFG

421 FVGSYASMGV YKFFRGPYWK ANMILTPILL PGAIFLLIVI MNFFLLFAHS SGVIPARSLF

481 FIILLWFLVS VPLSFAGSIV AHKQCNWDEH PTKTNQIARQ IPYQPWYLRT AQATLIAGIF

541 SFGSIAVELY FIYSSLWFNK IFYMFGFLLF SFLLLTLTTS LVTILITYYS LCLENWLWQW

601 RSFIIGGLGC SIYTFIHSIL FTKFKLGGVI TVVLYLGYSL IISALCCVVT GAIGFFSSMF

661 FIRKIYSAIK VE*
```

Using standard yeast molecular biology techniques, a TMN2 gene was disrupted by deleting essentially the entire coding sequence for TMN2, i.e., by deleting the nucleic acid sequence from 4 base-pair before the start codon to 10 base-pairs before the stop codon in both alleles of *S. cerevisiae*. All procedures were based on the publically available nucleic acid sequence of YDR107c, which is provided below as SEQ ID NO: 2 (5' to 3'):

```
ATGAAACGAAGTGTTTGGTTGCTGATTTATTGCTATGCAACTTTAACTAA

AGGATTTTCCTTGCCAGGCCTATCTCCCACAACATATCACTCAGGCGATG

AAATCCCGCTATTGGTGAACCGCTTGACTCCATCAATTTACTTTCAGCAT

CAAGATGAGGAAGGTAACGATGTTTCAGGCGATAAAGAACATTTTCTTTA

CTCCTATGATTACTATAATAAGAGGTTTCATTTTTGTAGACCAGAGCACG

TTGAGAAACAGCCGGAGTCGTTAGGTTCAGTCATATTTGGTGACAGAATT

TACAATTCCCCATTCCAATTGAACATGTTAGAGGAGAAAGAGTGTGTTGC

ACTTTGTAAAAGCACGATTCCGGGAAAAGATGCCAAATTTATCAACACGC

TTATTAAAAGTGGATTTTTCCAAAACTGGCTCGTGGATGGATTGCCAGCA

GCAAGAAAGGCTTATGATAGCAGAACAAAAACAAACTATTACGGCACAGG

ATTTGAGTTAGGTTTTACAGATGTTAAGCAAACCGTTGACGGTAAAGCAG

TTCCCAGTACGATGGAAGAGCTTACTTCAGAGGCCTCAAATGAGGATGTT

ATATTGGATGCTCGACAGCCCAAGAATGTTAAGCCTAATTTAGTTAAAAC

GGTAGAATTACCTTACTTTGTAAATCATTTTGACATTGAAGTGGAATTTC

ACGATCGTGGTAACGATAATTACCGAGTTGTTGGTGTCATTGTAAACCCT

GTATCTATCGAAAGATCGTCACCTGGCGCATGTTCTACAACGGGAAAACC

TCTGATACTAGACGAGGATAAGGATAACGAGGTTTACTTCACTTATTCTG

TTAAATTTGTTGCCTCTGATACAGTGTGGGCTACGAGATGGGATAAGTAT

CTACATATTTATGACCCGCAGATACAATGGTTTTCATTAATAAATTTTTC

CGTTATTGTTATTTTGTTGTCATCTGTTGTAATGCATTCTCTATTACGGG

CTTTGAAAAGCGATCTCGCTCGTTATAACGAACTGAACTTGGATAATGAA

TTCCATGAAGATTCTGGCTGGAAATTGGGCCATGGTGACGTATTTAGAAC

CCCATCTAAGTCGATGCTGCTATCCATTCTTGTGGGATCCGGTATGCAGT

TATTTTTGATGGTCATGTGTAGCATTTTTTTGCCGCAGTAGGTCTTGTG

TCGCCTGTTTCCAGAGGATCCCTGCCAACTGTAATGTTTGTTCTTTATGC

ATTATTTGGATTTGTAGGATCCTACGCCTCAATGGGTGTCTACAAATTTT

TTCGTGGACCCTATTGGAAGGCGAATATGATATTAACGCCAATATTACTT

CCTGGAGCAATTTTTTTACTGATTGTAATAATGAACTTCTTTTTGTTATT

TGCACATTCTTCAGGTGTCATCCCAGCGAGAAGCCTATTCTTTATCATTC

TTCTATGGTTTTTAGTTTCTGTTCCGTTGTCGTTTGCGGGTTCAATTGCT

GCTCATAAGCAGTGTAATTGGGATGAGCATCCAACTAAAACAAACCAAAT
```

```
                        -continued
CGCCAGACAGATTCCATATCAACCCTGGTACTTGAGAACAGCACAAGCAA

CCTTAATCGCTGGAATTTTCAGTTTCGGATCAATAGCGGTTGAGCTGTAC

TTCATTTACTCCAGTTTATGGTTCAACAAAATTTTTTATATGTTTGGATT

TTTACTCTTTTCATTCTTATTGTTGACCTTGACAACCTCATTAGTTACCA

TCTTGATCACATATTACTCGTTATGTCTAGAAAACTGGCTATGGCAATGG

AGAAGTTTTATTATTGGCGGTTTAGGATGTTCAATCTATACGTTCATCCA

CTCCATACTATTTACTAAGTTCAAGCTTGGTGGAGTTATTACTGTCGTGC

TCTATCTCGGATATTCACTTATTATATCTGCATTATGTTGTGTCGTCACT

GGAGCGATTGGTTTTTTTAGCAGTATGTTTTTTATTAGGAAGATATACTC

TGCCATTAAAGTTGAGTGA
```

The host yeast used to make the modified yeast cells was commercially available FERMAX™ Gold (Martrex, Inc., Chaska, MN, USA). Deletion of a TMN2 gene was confirmed by colony PCR. The modified yeast was grown in non-selective media to remove the plasmid conferring Kanamycin resistance used to select transformants, resulting in modified yeast that required no growth supplements compared to the parental yeast.

Example 2: Ethanol Production by Modified Yeast with Reduced Expression of TMN2 at 32° C.

Yeast harboring the deletion of the YDR107c gene were tested for their ability to produce ethanol compared to benchmark yeast (i.e., FERMAX™ Gold, herein "FG," which are wild-type for the YDR107c gene) in liquefact having a dry solid (DS) value of 34.2 and 35.5% dry solid at 32° C. Liquefact (i.e., corn flour slurry) was prepared by adding 600 ppm urea, 0.124 SAPU/g ds FERMGEN™ 2.5× (an acid fungal protease), 0.33 GAU/g ds CS4 (a variant of *Trichoderma reesei* glucoamylase) and 1.46 SSCU/g ds AKAA (*Aspergillus kawachii* α-amylase) at pH 5.2.

50 grams of liquefact was weighted into 100 ml vessels and inoculated with fresh overnight cultures from colonies of the FG-tmn2d strain or FG strain and incubated at 32° C. Samples were harvested by centrifugation at 55 hours, filtered through 0.2 μm filters, and analyzed for ethanol, glucose, and glycerol content by HPLC (Agilent Technologies 1200 series) using Bio-Rad Aminex HPX-87H columns at 55° C., with an isocratic flow rate of 0.6 ml/min in 0.01 N $H_2SO_4$ eluent. A 2.5 μl sample injection volume was used. Calibration standards used for quantification included known amounts of ethanol. The results of the analyses are shown in Table 2. Ethanol increase is reported with reference to the FG strain in the same condition.

TABLE 2

Analysis of fermentation broth following fermentation with FG-tmn2d and FG yeast

| Temp. (° C.) | DS (%) | Strain | Sampling time (hrs) | Glucose (g/L) | Glycerol (g/L) | Ethanol (g/L) | Ethanol increase (%) | Ethanol/DS |
|---|---|---|---|---|---|---|---|---|
| 32 | 34.2 | FG | 55 | 0.33 | 17.12 | 135.4 | n/a | 3.95 |
| 32 | 34.2 | FG-tmn2d | 55 | 0.34 | 16.68 | 138.65 | 1.024 | 4.05 |
| 32 | 35.5 | FG | 55 | 0.85 | 19.82 | 134.97 | n/a | 3.80 |
| 32 | 35.5 | FG-tmn2d | 55 | 0.42 | 19.35 | 137.49 | 1.019 | 3.87 |

Yeast harboring the deletion of the gene TMN2 (YDR107c) produced significantly more ethanol (i.e., up to 2.4%) compared to the reference strain in liquefact having higher value of DS at 32° C.

Example 3: Ethanol Production by Modified Yeast with Reduced Expression of TMN2 at 35° C.

Yeast harboring the deletion of the YDR107c gene were tested for their ability to produce ethanol compared to benchmark yeast (i.e., FERMAX™ Gold, herein "FG," which are wild-type for the YDR107c gene) in liquefact having a dry solid (DS) value of 35.8% dry solid at 35° C. Liquefact (i.e., corn flour slurry) was prepared by adding 600 ppm urea, 0.124 SAPU/g ds FERMGEN' 2.5× (an acid fungal protease), 0.33 GAU/g ds CS4 (a variant of *Trichoderma reesei* glucoamylase) and 1.46 SSCU/g ds AKAA (*Aspergillus kawachii* α-amylase) at pH 5.2.

50 grams of liquefact was weighted into 100 ml vessels and inoculated with fresh overnight cultures from colonies of the FG-tmn2d strain or FG strain and incubated at 35° C. Samples were harvested by centrifugation at 55 hours, filtered through 0.2 μm filters, and analyzed for ethanol, glucose, and glycerol content by HPLC (Agilent Technologies 1200 series) using Bio-Rad Aminex HPX-87H columns at 55° C., with an isocratic flow rate of 0.6 ml/min in 0.01 N $H_2SO_4$ eluent. A 2.5 μl sample injection volume was used. Calibration standards used for quantification included known amounts of ethanol. The results of the analyses are shown in Table 3. Ethanol increase is reported with reference to the FG strain in the same condition.

TABLE 3

Analysis of fermentation broth following fermentation
with FG-tmn2d and FG yeast at 35° C.

| Temp. (° C.) | DS (%) | Strain | Sampling time (hrs) | Glucose (g/L) | Glycerol (g/L) | Ethanol (g/L) | Ethanol increase (%) | Ethanol/ DS |
|---|---|---|---|---|---|---|---|---|
| 35 | 35.8 | FG | 55 | 48.2 | 14.91 | 124.85 | n/a | 3.49 |
| 35 | 35.8 | FG-tmn2d | 55 | 45.5 | 14.74 | 127.94 | 1.024 | 3.57 |

Yeast harboring the deletion of the gene TMN2 (YDR107c) produced significantly more ethanol (i.e., up to 2.4%) compared to the reference strain in liquefact having higher value of DS at 35° C.

What is claimed is:

1. Modified yeast cells derived from parental yeast cells, the modified cells comprising a genetic alteration that causes the modified cells to produce a decreased amount of functional TMN2 polypeptide compared to the parental cells, wherein the modified cells produce during fermentation an increased amount of ethanol compared to parental cells under equivalent fermentation conditions; and wherein the modified cells further comprise an exogenous gene encoding a carbohydrate processing enzyme.

2. The modified cells of claim 1, wherein the genetic alteration comprises a disruption of a YDR107C gene present in the parental cells.

3. The modified cells of claim 2, wherein disruption of a YDR107C gene is the result of deletion of all or part of a YDR107C gene.

4. The modified cells of claim 2, wherein disruption of a YDR107C gene is the result of deletion of a portion of genomic DNA comprising a YDR107C gene.

5. The modified cells of claim 2, wherein disruption of a YDR107C gene is the result of mutagenesis of a YDR107C gene.

6. The modified cells of claim 2, wherein disruption of a YDR107C gene is performed in combination with introducing a gene of interest at the genetic locus of a YDR107C gene.

7. The modified cells of claim 1, wherein the cells do not produce functional TMN2 polypeptides.

8. The modified cells of claim 1, wherein the cells do not produce TMN2 polypeptides.

9. The modified cells of claim 1, wherein the carbohydrate processing enzyme is an alpha-amylase, an glucoamylase, or a trehalase.

10. The modified cells of claim 1, further comprising an alteration in the glycerol pathway and/or the acetyl-CoA pathway.

11. The modified cells of claim 1, further comprising an alternative pathway for making ethanol.

12. The modified cells of claim 1, wherein the cells are of a *Saccharomyces* spp.

13. A method for producing an alcohol fermentation product comprising: fermenting a carbohydrate substrate with the modified yeast cell of claim 1.

14. The method of claim 13, wherein the genetic alteration comprises disruption of a YDR107C gene in the parental cells by genetic manipulation.

15. The method of claim 14, wherein disruption of a YDR107C gene is performed in combination with introducing a gene of interest at the genetic locus of a YDR107C gene.

16. The method of claim 14, wherein disruption of a YDR107C gene is performed in combination with making an alteration in the glycerol pathway and/or the acetyl-CoA pathway.

17. The method of claim 14, wherein disruption of a YDR107C gene is performed in combination with adding an alternative pathway for making ethanol.

18. The method of claim 13, wherein the genetic alteration comprises deletion of a YDR107C gene in the parental cells using genetic manipulation.

19. The method of claim 13, wherein the modified cell is from a *Saccharomyces* spp.

\* \* \* \* \*

SEQUENCE LISTING

<160> NUMBER OF SEQ ID NOS: 2

<210> SEQ ID NO 1
<211> LENGTH: 672
<212> TYPE: PRT
<213> ORGANISM: Saccharomyces cerevisiae

<400> SEQUENCE: 1

Met Lys Arg Gly Val Trp Leu Leu Ile Tyr Cys Tyr Ala Thr Leu Thr
1               5                   10                  15

Lys Gly Phe Ser Leu Pro Gly Leu Ser Pro Thr Thr Tyr His Ser Gly
            20                  25                  30

Asp Glu Ile Pro Leu Leu Val Asn Arg Leu Thr Pro Ser Ile Tyr Phe
        35                  40                  45

Gln His Gln Asp Glu Glu Gly Asn Asp Val Ser Gly Asp Lys Glu His
    50                  55                  60

Phe Leu Tyr Ser Tyr Asp Tyr Tyr Asn Lys Arg Phe His Phe Cys Arg
65                  70                  75                  80

Pro Glu His Val Glu Lys Gln Pro Glu Ser Leu Gly Ser Val Ile Phe
                85                  90                  95

Gly Asp Arg Ile Tyr Asn Ser Pro Phe Gln Leu Asn Met Leu Glu Glu
            100                 105                 110

Lys Glu Cys Val Ala Leu Cys Lys Ser Thr Ile Pro Gly Lys Asp Ala
        115                 120                 125

Lys Phe Ile Asn Thr Leu Ile Lys Ser Gly Phe Phe Gln Asn Trp Leu
    130                 135                 140

Val Asp Gly Leu Pro Ala Ala Arg Lys Ala Tyr Asp Ser Arg Thr Lys
145                 150                 155                 160

Thr Asn Tyr Tyr Gly Thr Gly Phe Glu Leu Gly Phe Thr Asp Val Lys
                165                 170                 175

Gln Thr Val Asp Gly Lys Ala Val Pro Ser Thr Met Glu Glu Leu Thr
            180                 185                 190

Ser Glu Ala Ser Asn Glu Asp Val Ile Leu Asp Ala Arg Leu Pro Lys
        195                 200                 205

Asn Val Lys Pro Asn Leu Val Lys Thr Val Glu Leu Pro Tyr Phe Val
    210                 215                 220

Asn His Phe Asp Ile Glu Val Glu Phe His Asp Arg Gly Asn Asp Asn
225                 230                 235                 240

Tyr Arg Val Val Gly Val Ile Val Asn Pro Val Ser Ile Glu Arg Ser
                245                 250                 255

Ser Pro Gly Ala Cys Ser Thr Thr Gly Lys Pro Leu Ile Leu Asp Glu

```
            260                 265                 270
Asp Lys Asp Asn Glu Val Tyr Phe Thr Tyr Ser Val Lys Phe Val Ala
            275                 280                 285

Ser Asp Thr Val Trp Ala Thr Arg Trp Asp Lys Tyr Leu His Ile Tyr
        290                 295                 300

Asp Pro Gln Ile Gln Trp Phe Ser Leu Ile Asn Phe Ser Val Ile Val
305                 310                 315                 320

Ile Leu Leu Ser Ser Val Val Met His Ser Leu Leu Arg Ala Leu Lys
                325                 330                 335

Ser Asp Leu Ala Arg Tyr Asn Glu Leu Asn Leu Asp Asn Glu Phe His
            340                 345                 350

Glu Asp Ser Gly Trp Lys Leu Gly His Gly Asp Val Phe Arg Thr Pro
        355                 360                 365

Ser Lys Ser Met Leu Leu Ser Ile Leu Val Gly Ser Gly Met Gln Leu
    370                 375                 380

Phe Leu Met Val Met Cys Ser Ile Phe Phe Ala Ala Val Gly Leu Val
385                 390                 395                 400

Ser Pro Val Ser Arg Gly Ser Leu Pro Thr Val Met Phe Val Leu Tyr
                405                 410                 415

Ala Leu Phe Gly Phe Val Gly Ser Tyr Ala Ser Met Gly Val Tyr Lys
            420                 425                 430

Phe Phe Arg Gly Pro Tyr Trp Lys Ala Asn Met Ile Leu Thr Pro Ile
        435                 440                 445

Leu Leu Pro Gly Ala Ile Phe Leu Leu Ile Val Ile Met Asn Phe Phe
    450                 455                 460

Leu Leu Phe Ala His Ser Ser Gly Val Ile Pro Ala Arg Ser Leu Phe
465                 470                 475                 480

Phe Ile Ile Leu Leu Trp Phe Leu Val Ser Val Pro Leu Ser Phe Ala
                485                 490                 495

Gly Ser Ile Val Ala His Lys Gln Cys Asn Trp Asp Glu His Pro Thr
            500                 505                 510

Lys Thr Asn Gln Ile Ala Arg Gln Ile Pro Tyr Gln Pro Trp Tyr Leu
        515                 520                 525

Arg Thr Ala Gln Ala Thr Leu Ile Ala Gly Ile Phe Ser Phe Gly Ser
    530                 535                 540

Ile Ala Val Glu Leu Tyr Phe Ile Tyr Ser Ser Leu Trp Phe Asn Lys
545                 550                 555                 560

Ile Phe Tyr Met Phe Gly Phe Leu Leu Phe Ser Phe Leu Leu Leu Thr
                565                 570                 575

Leu Thr Thr Ser Leu Val Thr Ile Leu Ile Thr Tyr Tyr Ser Leu Cys
            580                 585                 590

Leu Glu Asn Trp Leu Trp Gln Trp Arg Ser Phe Ile Ile Gly Gly Leu
        595                 600                 605

Gly Cys Ser Ile Tyr Thr Phe Ile His Ser Ile Leu Phe Thr Lys Phe
    610                 615                 620

Lys Leu Gly Gly Val Ile Thr Val Val Leu Tyr Leu Gly Tyr Ser Leu
625                 630                 635                 640

Ile Ile Ser Ala Leu Cys Cys Val Val Thr Gly Ala Ile Gly Phe Phe
                645                 650                 655

Ser Ser Met Phe Phe Ile Arg Lys Ile Tyr Ser Ala Ile Lys Val Glu
            660                 665                 670

<210> SEQ ID NO 2
```

```
<211> LENGTH: 2019
<212> TYPE: DNA
<213> ORGANISM: Saccharomyces cerevisiae

<400> SEQUENCE: 2
atgaaacgaa gtgtttggtt gctgatttat tgctatgcaa ctttaactaa aggattttcc        60
ttgccaggcc tatctcccac aacatatcac tcaggcgatg aaatcccgct attggtgaac       120
cgcttgactc catcaattta ctttcagcat caagatgagg aaggtaacga tgtttcaggc       180
gataaagaac attttctta ctcctatgat tactataata agaggtttca tttttgtaga        240
ccagagcacg ttgagaaaca gccggagtcg ttaggttcag tcatatttgg tgacagaatt       300
tacaattccc cattccaatt gaacatgtta gaggagaaag agtgtgttgc actttgtaaa       360
agcacgattc cgggaaaaga tgccaaattt atcaacacgc ttattaaaag tggattttc        420
caaaactggc tcgtggatgg attgccagca gcaagaaagg cttatgatag cagaacaaaa       480
acaaactatt acggcacagg atttgagtta ggttttacag atgttaagca aaccgttgac       540
ggtaaagcag ttcccagtac gatggaagag cttacttcag aggcctcaaa tgaggatgtt       600
atattggatg ctcgacagcc caagaatgtt aagcctaatt tagttaaaac ggtagaatta       660
ccttactttg taaatcattt tgacattgaa gtggaatttc acgatcgtgg taacgataat       720
taccgagttg ttggtgtcat tgtaaaccct gtatctatcg aaagatcgtc acctggcgca       780
tgttctacaa cgggaaaacc tctgatacta gacgaggata aggataacga ggtttacttc       840
acttattctg ttaaatttgt tgcctctgat acagtgtggg ctacgagatg ggataagtat       900
ctacatattt atgacccgca gatacaatgg ttttcattaa taattttttc cgttattgtt       960
attttgttgt catctgttgt aatgcattct ctattacggg ctttgaaaag cgatctcgct      1020
cgttataacg aactgaactt ggataatgaa ttccatgaag attctggctg gaaattgggc      1080
catggtgacg tatttagaac cccatctaag tcgatgctgc tatccattct tgtgggatcc      1140
ggtatgcagt tatttttgat ggtcatgtgt agcattttt ttgccgcagt aggtcttgtg       1200
tcgcctgttt ccagaggatc cctgccaact gtaatgtttg ttctttatgc attatttgga      1260
tttgtaggat cctacgcctc aatgggtgtc tacaaatttt ttcgtggacc ctattggaag      1320
gcgaatatga tattaacgcc aatattactt cctggagcaa ttttttttact gattgtaata      1380
atgaacttct ttttgttatt tgcacattct tcaggtgtca tcccagcgag aagcctattc      1440
tttatcattc ttctatggtt tttagtttct gttccgttgt cgtttgcggg ttcaattgct      1500
gctcataagc agtgtaattg ggatgagcat ccaactaaaa caaaccaaat cgccagacag      1560
attccatatc aaccctggta cttgagaaca gcacaagcaa ccttaatcgc tggaattttc      1620
agtttcggat caatagcggt tgagctgtac ttcatttact ccagtttatg gttcaacaaa      1680
attttttata tgtttggatt tttactcttt tcattcttat tgttgacctt gacaacctca      1740
ttagttacca tcttgatcac atattactcg ttatgtctag aaaactggct atggcaatgg      1800
agaagtttta ttattggcgg tttaggatgt tcaatctata cgttcatcca ctccatacta      1860
tttactaagt tcaagcttgg tggagttatt actgtcgtgc tctatctcgg atattcactt      1920
attatatctg cattatgttg tgtcgtcact ggagcgattg gttttttttag cagtatgttt      1980
tttattagga agatatactc tgccattaaa gttgagtga                             2019
```